US011056216B2

(12) United States Patent
Opler et al.

(10) Patent No.: US 11,056,216 B2
(45) Date of Patent: Jul. 6, 2021

(54) SYSTEM FOR GUIDING CLINICAL DECISIONS USING IMPROVED PROCESSING OF DATA COLLECTED DURING A CLINICAL TRIAL

(71) Applicant: MedAvante-ProPhase, Inc., Hamilton, NJ (US)

(72) Inventors: Mark G. A. Opler, Hamilton, NJ (US); Sofija Jovic, Hamilton, NJ (US)

(73) Assignee: MedAvante-ProPhase, Inc., Hamilton, NJ (US)

( * ) Notice: Subject to any disclaimer, the term of this patent is extended or adjusted under 35 U.S.C. 154(b) by 609 days.

(21) Appl. No.: 15/656,924

(22) Filed: Jul. 21, 2017

(65) Prior Publication Data
US 2018/0025133 A1   Jan. 25, 2018

Related U.S. Application Data

(60) Provisional application No. 62/365,122, filed on Jul. 21, 2016.

(51) Int. Cl.
*G16H 10/20*   (2018.01)
*G16H 50/20*   (2018.01)
(Continued)

(52) U.S. Cl.
CPC ............ *G16H 10/20* (2018.01); *G16H 10/60* (2018.01); *G16H 50/20* (2018.01); *G16H 15/00* (2018.01)

(58) Field of Classification Search
CPC ........ G16H 10/20; G16H 50/20; G16H 10/60; G16H 15/00; G06F 19/321; G06F 19/3418
See application file for complete search history.

(56) References Cited

U.S. PATENT DOCUMENTS

2007/0292012 A1   12/2007  Brandon et al.
2008/0114689 A1*  5/2008   Psynik ............... H04L 63/0272
                                           705/51
(Continued)

FOREIGN PATENT DOCUMENTS

WO    WO 99/63473        12/1999
WO    WO 01/93178 A2     12/2001

OTHER PUBLICATIONS

Aldukheil, Maher A., Developing a Systematic Architecture Approach for Designing an Enhanced Electronic Medical Record (EEMR) System (2013), Lawrence Technological University, ProQuest Dissertations Publishing, 2013. 3560401 (Year: 2013).*

*Primary Examiner* — Fonya M Long
*Assistant Examiner* — Brandon Chu
(74) *Attorney, Agent, or Firm* — Morgan, Lewis & Bockius, LLP

(57) ABSTRACT

A system for providing improved processing of data collected during a clinical trial. The system includes a portable electronic device configured to be operated by a clinician and/or a patient. The portable electronic device is configured for collecting data related to the condition of the patient participating in the clinical trial. The system also includes a controller for processing data collected from the patient. The data received from the patient includes AV data, bio sensor data, and clinician data based on information inputted into the portable electronic device by the clinician in response to an interview of the patient. The controller is configured to process the AV, bio data sensor and clinician data and output a recommended course of action related to the patient's participation in the clinical trial based on the data received from the patient.

4 Claims, 2 Drawing Sheets

(51) Int. Cl.
*G16H 10/60* (2018.01)
*G16H 15/00* (2018.01)

(56) References Cited

U.S. PATENT DOCUMENTS

| | | | |
|---|---|---|---|
| 2008/0270420 A1 | 10/2008 | Rosenberg | |
| 2011/0178820 A1* | 7/2011 | Soni | A61B 5/0002 |
| | | | 705/3 |
| 2011/0261194 A1 | 10/2011 | Udani | |
| 2012/0323590 A1* | 12/2012 | Udani | G16H 10/60 |
| | | | 705/2 |
| 2013/0054262 A1* | 2/2013 | Edwards | G16H 20/10 |
| | | | 705/2 |
| 2017/0228501 A1* | 8/2017 | Turner, Jr. | H04L 67/18 |

* cited by examiner

SYSTEM FOR GUIDING CLINICAL DECISIONS USING IMPROVED PROCESSING OF DATA COLLECTED DURING A CLINICAL TRIAL

This application is a Non-Provisional application of U.S. Provisional Application No. 62/365,122, filed Jul. 21, 2016, of which is incorporated herein by reference in the entirety.

SUMMARY

The application relates to a system and method for guiding and improving clinical decisions based on data obtained during a clinical trial. The system and method utilizes and integrates the data collected to guide and improve the clinical decisions.

The data is collected from several sources such as, for example, ratings of the clinical interview conducted by the clinician of the patient, collected using an Electronic Clinical Outcome Assessment (eCOA) platform. The eCOA platform includes an electronic adaptation of rating scales, questionnaires, interview guides, and other instruments used to derive a rating of a patient's duration, type, or severity of illness, or to arrive at a categorized or spectrum-oriented diagnosis. These measures may be owned by third parties (publishers and authors) or in the public domain, but the method of their electronic adaptation is innovative and unique and encompasses an integral part of the system and method described herein. The data may also include audio and/or video (AV) recording of an interview with a patient. Another example, of data that may be collected is biosensor data collected at the assessment or between assessments using, for example, continuous measurement methods using commercial-off-the-shelf or research-grade devices (e.g. FitBit, BioStamp, etc.) or application-generated data from smartphones.

The system may also include collecting metadata (the term "metadata" as used herein refers to collected data that provides information regarding an aspect of the patient and/or clinician) from a handheld device (e.g., an iPad or a Windows Surface tablet) on which a clinician records observations and rates symptoms during an clinical, behavioral, or neuropsychological assessment of a patient. The system disclosed herein includes an innovative way of integrating the collected data in order to guide clinical decision making. For example, the collected metadata—which represents a quantification of the clinician's interaction patterns with the device in the process of collecting patient data (audio, video, biometric or otherwise)—is not currently being used in any conventional systems that attempt to guide clinical decisions.

The system and method may be used in any standardized patient assessment or treatment modality, such as evidence-based diagnosis or treatment in healthcare or research visits in clinical trials. The system may be used to improve clinical decisions in several different ways. For example, in one embodiment, the collected data may be analyzed and feedback may be provided to a clinician in real time and/or when the clinician is reviewing the collected information from an assessment and making, for example, a final and/or assessment. The feedback provided by the system can improve the accuracy of the clinician's diagnosis or improve the rating of change over time.

According to another embodiment, the system may be used in a situation where there is independent diagnostic adjudication or a second clinical opinion. The system may integrate and analyze the data to present the independent clinician who is completing the review/adjudication with a risk-adjusted dashboard of information and improve the comprehensiveness and effectiveness, as well as the efficiency of the review being conducted.

According to yet another embodiment, the system utilizes data (e.g., answers, metadata, etc.) that the patient provides by interacting with an Electronic Patient Reported Outcomes (ePRO) component of an eCOA platform. The ePRO refers to a specific subset of information that is provided directly by the patient. These patient reported outcomes may result from the patient responding to symptom severity questionnaires or by providing quality of life measures, for example. These outcomes are self-reported by the patient, and are distinct from any outcomes that are completed by a clinician on a professional assessment of the patient. The ePRO may be provided on a handheld device (e.g. a Samsung Galaxy) that is provided to the patient. The device may contain the patient module portion of an eCOA platform. The ePRO module includes appropriate questionnaires, instructions, and edit-checks to support the patient's efforts to provide the requested information. The system utilizes not only the data provided from the patient answers, but also the way the patient provide those answers and, also, the way the patient interacts with the device to assess the reliability of their answers and provide the research/treating clinician with additional information about motivation of the patient and other factors that may influence their participation in study or treatment.

BRIEF DESCRIPTION OF THE DRAWINGS

The features, aspects, and advantages of the present invention will become apparent from the following description, and the accompanying exemplary embodiments shown in the drawings, which are briefly described below.

DETAILED DESCRIPTION

Figure 1:
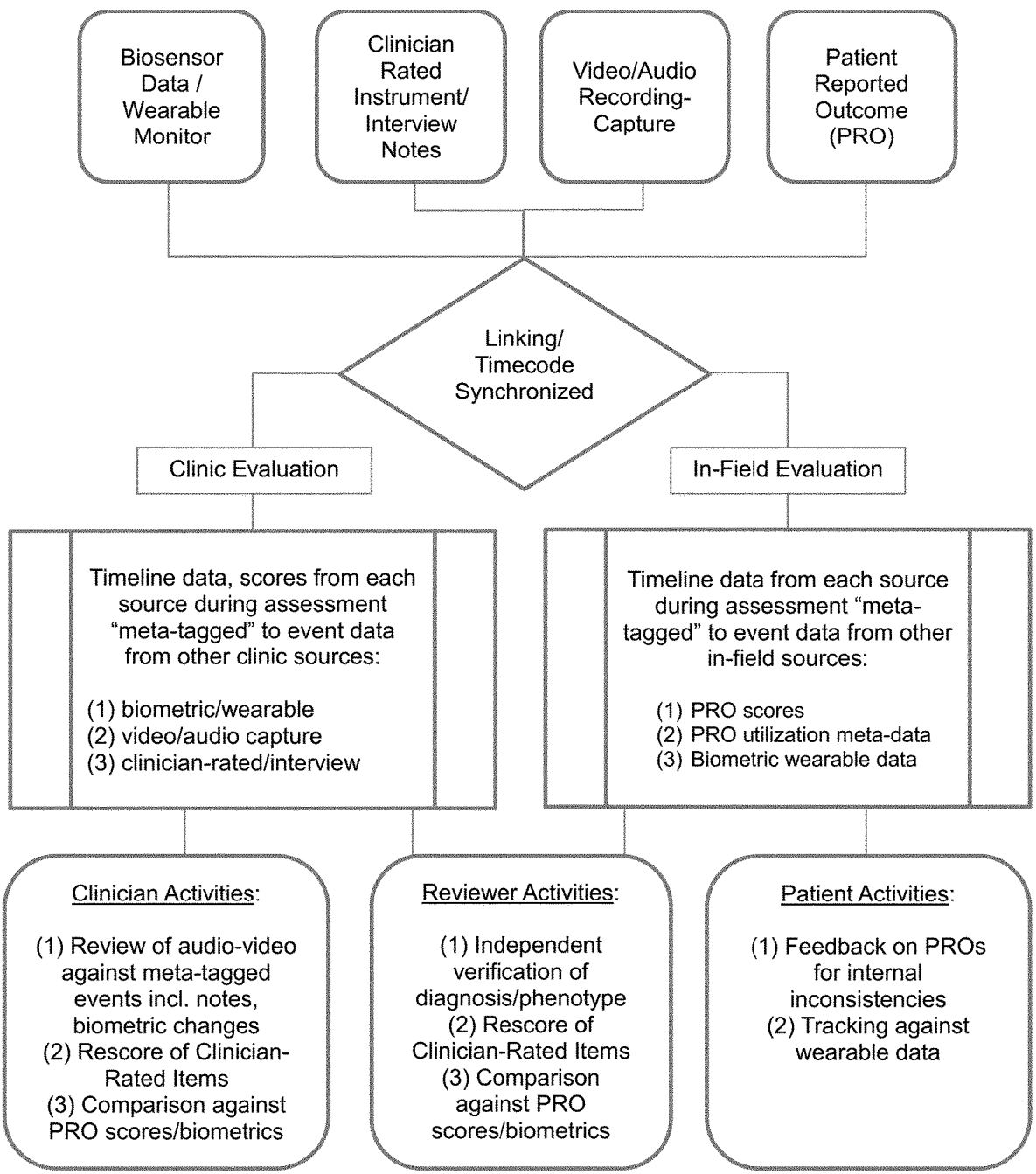
FIG. 1 is a diagram showing the data input, processing, analysis, output and including the patient and clinician interaction with an exemplary system of the present disclosure.

The following describes how the system is set up to provide a method for providing in vivo clinical feedback to the clinician assessing a patient during a clinical trial, for example. The eCOA platform may be loaded on to a mobile or stationary device that includes a processor and a display. The clinician may interact and direct the operation of the eCOA platform using the display (e.g., touch screen) or via a separate mouse or keyboard, for example. The system preferably includes security protection for the eCOA platform that requires the clinician to, for example, enter a user ID and password.

After gaining access to the platform the clinician may initiate an AV recording of a patient interview. The recording may be conducted directly by the audio visual capturing technology on the device, or by a separate device(s) that is coupled (e.g., via wireless or direct connection) to the clinician's device. The platform is configured to provide the clinician with the appropriate instruments/scales that need to be administered to the patient. As described herein, "patient" may refer to any subject/participant, including patient's caregiver, depending on the requirements of the particular instrument/rating scale. The clinician uses that mobile device (e.g., a tablet) to record notes and scores collected during the assessment. The platform may also be receiving data from other sources, such as from biosensors attached to the patient at the time of the interview or in the reporting period prior (i.e. between visits). These sensors may report on continuously measured, passive variables, such as the skin galvanic response, heartbeat, temperature, motion (tremors, tapping), sleep (obtained, for example, over the course of a day or a week), etc. The platform analyzes the sensors and provides the clinician with certain selected and appropriate analyzed output of these continuous measurement devices. In addition to analyzing patient, caregiver, and clinician-rated outcomes, and integrating those with biometric data from a wearable sensor, the platform synthesizes data in view of a plurality of factors, including but not limited to the disease being treated, a course of treatment for the disease and risk coefficients, to produce metadata and in response to the metadata, produce a clinically actionable outcome, such as screening a patient in or out of a clinical trial, randomizing them into a particular arm, triggering a safety protocol, or simply providing the research clinician with a quantified estimate of the patient's propensity for dropout from study or of exhibiting high levels of placebo response. An arm is a group or subgroup of participants in a clinical trial that receives specific interventions, or no intervention, according to the study protocol.

Currently, there is no system on the market that integrates inputs from all of these data sources and, using a series of calculations and probabilistic equations (such as Bayesian modeling) based on the plurality of factors, delivers an actionable, and validated clinical decision. Another unique feature is the use of metadata in this process. Metadata includes patient and clinician interactions with the device, such as how long an assessment took, which fields were used and in what way, what was the response latency, which items were changed, et cetera, and this information is overlaid on AV timecode data and other data inputs to provide context to the data that is not currently available. For example, in a clinical trial in which the primary outcome is a frequency count of seizures as reported by caregivers, a level of risk may be assigned to the data that varies based on the time distance between the incident itself and the time of the report and further refine the assessment of accuracy as data is gathered on the average performance of that patient as a reliable reporter. The process may also function to provide the clinician with consolidated information, before, during, or after the clinical interview, containing patient reported outcomes and associated metadata that the patient completed prior to the visit. The data collected may be stored on the mobile device or on a remote storage location that may be accessed by the device using conventional and secure technology (such as, network, internet, cloud, etc.).

Figure 2:
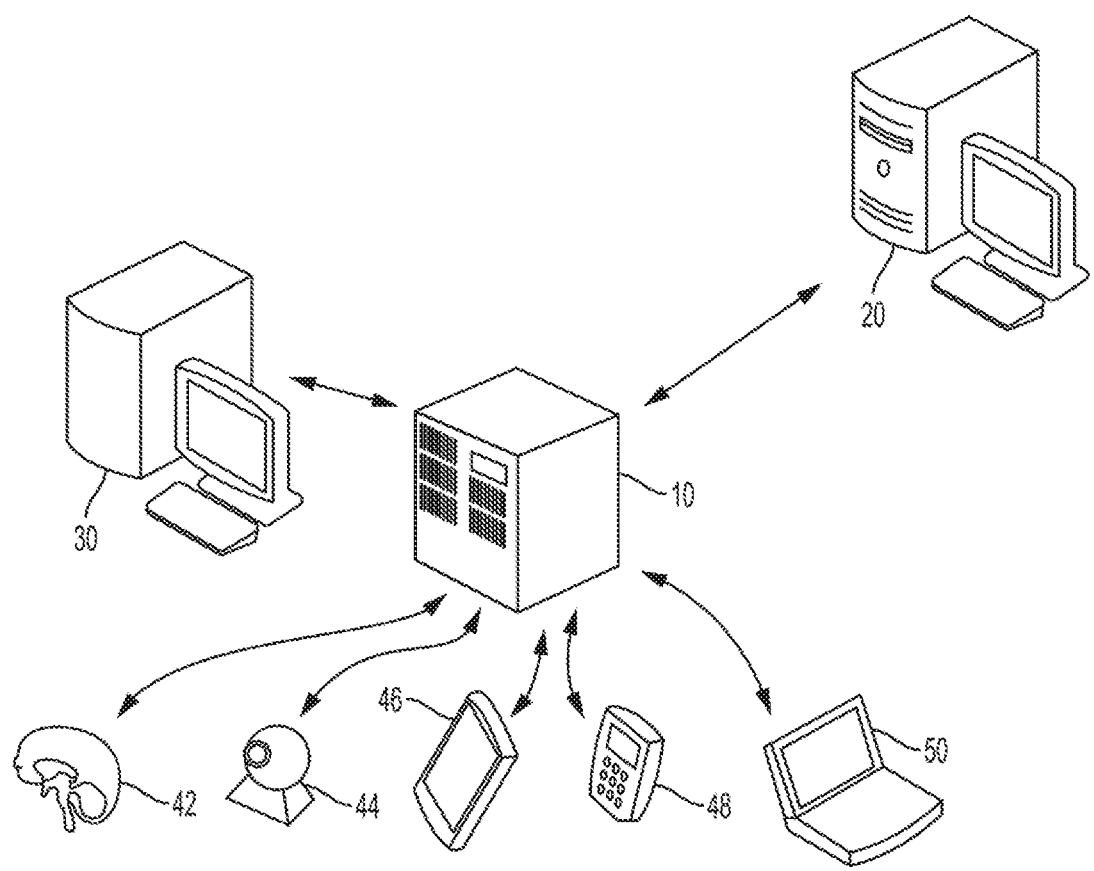
FIG. 2 shows a diagram of hardware components of an exemplary system of the present disclosure.

As shown in FIG. 2, a system as described herein may include a central data hub or controller 10. The controller is operatively connected to a plurality of components including an output terminal 20 and a control terminal 30. The output terminal 20 may include a controller (i.e., processor), a display and/or a printer. The output terminal is configured to produce reports and information to be used by personnel (e.g., clinicians, patients, etc.) involved in the clinical study. The control terminal 30 may include a controller (i.e., processor), a display and/or a printer. The control terminal 30 is configured to permit a user to interface with the system to request reports and data, for example, and to permit change of the analysis being done by the central data hub or controller 10. Each of the central data hub, output terminal 20 and a control terminal may perform the main processing function of the system and may be integrated into one or more stations depending on the system configuration.

The system may also include various components for collecting data such as a medical measurement device 48, a biometric sensor 42, a user interface device 46, 50, a camera (video, audio, or holographic) 44. The hardware system may comprise more than one of any of the foregoing components. Each of the aforementioned components (10, 20, 30, 42, 44, 46, 48, 50) may be a distinct device and may comprise additional hardware and/or software components. For example, the system may include the camera 44, and the camera 44 may comprise its own processor and wireless connection to the system. As another example, the user interface device 46, 50 may comprise a touch screen equipped with internal accelerometers that respond to shaking and rotations of the touch screen.

The camera 44 may provide still or moving pictures or holograms and be used to verify the identity of subjects, doctors, and study materials, and to provide general source recording of medical and clinical activities. The camera 44 may also comprise microphone for audio receiving and recording capabilities.

One or more components may be combined into a single device that may form all or part of the system. For example, the medical measurement device 48, the interface device 46, the camera 44 may be combined in one embodiment of the present system in a common housing such as that of a tablet computer 50. The system may, optionally, include a printer for printing out documents on paper or on other media. As stated above, the system may be connected to via a network connection to a remote database or control terminal housed remotely in a server or cloud. The components of the system may be connected via local area network (LAN), Wi-Fi, BLUETOOTH®, WiMAX, MIT-2000, satellite, cellular network, wide area network (WAN), or the Internet.

The central data hub, controller or processor 10 may serve to exercise common control of operations of the components associated with the system. The central controller 10 may either be a conventional processor, in which case instructions for operation of the other components of the present system are stored in memory or in other computer readable storage media, or alternatively the processor 10 can be a special purpose processor with instructions included in read-only memory or other hardware. The functions of the central data hub or processor 10 may be shared with other components of the system (e.g., terminals 20, 30 or portable computers 46, 50) that may optionally include processing capability. For example, an eCOA system may include processing functions on the clinician's tablet or at a remote controller.

In one embodiment, the central data hub includes a processor that is included in a computer, and a display device such as a computer screen that can be associated with the computer. Alternatively or in addition, the processor can be placed in communication with an external computer (20, 30) or other device for inputting clinical trial information, which can be stored in memory in the system and/or directly uploaded from the system to a clinical trial database.

The system may also contain one or more computer-readable storage medium for the storage of instructions or storage of a database for the execution of the assessments and other methods disclosed herein. The computer-readable medium may comprise, for example, random access memory (RAM), non-volatile memory (NVM), a hard drive, or a cloud storage.

As described in detail throughout this disclosure, the system may be configured to collect data directly (via wired or wireless connection) from a variety of medical measurement devices 48. The measurement device 48 may be a mobile health device including but not limited to a sphygmomanometer, glucometer, pulse oximeter, thermometer, pedometer, electrocardiogram, biofeedback device, actimeter, optical refractor, stethoscope, pulmonary function test device, urine analyzer, and exhaled gas analyzer. Each of these devices may have its own processor and communication hardware to send measurement results to the system. The medical devices can be devices used in a clinic for making clinical study related measurements. For example, one medical device may be a scale that transmits the weight of remaining test material brought back by a subject into the system. As another example, the medical device can be an automated pill counter to be used to count the number of pills given to and received back from a subject.

Alternatively, or in addition to receiving data from the medical devices, the system may be configured to collect data and/or reports directly or indirectly from laboratory and medical facilities using an interface for medical assessments. The laboratory and medical facilities include but are not limited to analytic laboratories, surgeries, pathology, dermatology, gastroenterology, cardiology, obstetrics, gynecology, oncology, orthopedics, pediatrics, internal medicine, sleep medicine, radiology, and urology. The medical assessments may include analytical laboratory tests, specialist assessments, procedures, reports, and others. Collection of data or assessments from the external laboratories and medical facilities can be by direct data importation or indirectly by scanning in a paper report, which may involve optical character recognition or manual capture of data fields. The laboratories include, for example, in-house lab instruments located at the clinical trial site that can communicate results of measurements directly to the system.

The system may comprise a biometric sensor 42, which can be one or more of a number of known devices that can record heart rate, blood pressure, energy expenditure, etc. The sensor 42 may be wearable or affixed to the person.

The user interface device 46 of the hardware system may be one or more of a monitor, computer screen, holographic screen, touch pad, keyboard, mouse, trackball, joystick, pointing stick, stylus, touch screen, light pen, eye tracking device, steering wheel, paddle, dancepad, laser pen, camera, microphone, voice-to-text, and text-to-voice conversion system, augmented reality device, screenless display, interactive display, and others for a user to interface with the system. The user interface device 46 may be a screen, a display, a screenless display, a touchscreen, or a interactive display. A screenless display may comprise a visual image display (e.g., hologram, virtual reality goggles, heads up display), virtual retina display (e.g., retinal projector), or synaptic interface.

The platform loaded on the user interface device may include software that allows the clinician to take certain actions during the assessment such as, for example, make handwritten or typed notes, to record their notes, pull up references (e.g. interview prompts), and to provide initial scores. In addition to this directly-provided data, the device may include software that captures passively-collected metadata about the clinician's use of the device. This includes time-stamping every note that the clinician makes and associating it with a section of the AV/Bio data. Thus, the system provides for tagging the video/audio and biosensor data stream with the clinicians' note taking or other interaction with the device.

After the clinician completes interacting with the patient, and before the final scores are submitted, the system provides basic edit checks that are performed to ensure that there are no missing or impossible values (e.g. score of 7 on a scale limited to values of 1-5). The system may use the tags of the AV/Bio data stream or biometric data stream to provide the clinician with an annotated recording of the interview of the patient. This annotated/tagged version of the AV/Bio data stream may be used in multiple ways to guide clinician's final scoring. For example, if the clinician struggles with making an appropriate entry related to a particular item on the instrument/questionnaire, the clinician can easily pull up the section of the video that has been automatically tagged as associated with the notes that the clinician made on that item.

The system may also be configured to require that the clinician review certain interview sections before the clinician is permitted to change a score on a subjective item. The system may also be configured to use the information about inherent reliability of different scale components to require that the particular section of the AV/Bio recording (as identified by the metadata) be reviewed prior to scoring particular items. In addition, the system may use data collected from various biometric sensors and calculate trends such as, for example, changes in heartrate over the course of the assessment. These trends may be valuable in helping to better understand patient conditions, ruling in or ruling out different phenotypes. The results of various "challenge tests" including, for example, biopsychosocial stress tests and tests of reactions to visual or audio stimuli in real time may also be collected by the system and used to guide the clinician in providing appropriate scoring.

The system may also be configured to identify any discrepancies between the patient reported outcomes (PROs) and the clinician's assessment. For example, a clinician may rate a patient as severely depressed, but the patient reports improvements in depressive symptoms throughout the week. These apparent conflicts or discrepancies between outcome and assessment may be flagged as discrepant and provided to the clinician during the interview to enable the clinician to query the patient further, or after the interview to allow the clinician to integrate that patient report into their final rating. In addition, the system may be configured to compare and analyze the data collected from multiple sensors and sources for discrepancies. For example, if the in-field biosensor that the patient wore over the course of the week measured improved sleep patterns but the patient complains of worsening sleep symptoms, the system could prompt the clinician (e.g., on the device display) with relevant information during the interview in order to resolve the discrepancy and improve the assessment.

As described above, the system and method disclosed herein is configured to integrate data received from multiple sources, in an automated, validated, and real-time way, in order to improve assessment, diagnosis and treatment by providing risk-adjusted, actionable information to the clinician at the time of their clinical evaluation.

The system and method also provides for an improved diagnostic adjudication and/or independent checking of the results of the clinician's analysis. In many research and some clinical practice instances, there is a need for independent review of the clinician's work. The independent review can be used for several purposes such as, for example: (1) independent review of eligibility of a patient to be included in a clinical trial, (2) diagnostic adjudication/confirmation of a diagnosis by an independent clinician, (3) quality control and/or training of the clinician, (4), assessing and documenting adherence of the clinician to a standardized diagnosis or treatment regimen, and (5) functional unblinding during double-blind research.

Functional unblinding refers to those situations in which the research clinician is not able to remain "blinded" to the assignment of the patient to a particular arm of treatment. When patients enter clinical research, they are often randomly assigned ("randomized") to one of the standard available treatment, placebo, or the novel treatment being studied. However, either the standard treatment or the novel treatment may have marked side effects that would make inadvertently signal to the clinician which of the research conditions the patient was assigned to. An example of such a side effect may be marked, rapid weight gain. Thus, during testing of a new antipsychotic medication that would reduce the weight gain, a clinician would assume that a patient's failure to gain the usual amount of weight is due to the patient being likely assigned to the novel treatment, and this may influence their assessment of the efficacy of treatment. In instances where functional unblinding is a concern, regulatory agencies often require that the research sponsor demonstrate that the patient assessment was done remotely or in some other way that prevents the assessor from witnessing the "unblinding" aspects of the patient's clinical presentation.

When the assessment data is collected, the available data streams may be analyzed to determine the risk or likelihood that the score or assessment does not accurately reflect the patient's outcome. The system may provide for the data that is provided to an independent reviewer may be completely blinded, i.e., the reviewer receives the same information that the original clinician did and is asked to provide an independent assessment. The system may be configured to compare the two assessments for congruence or discrepancies and identify the assessments for further review if needed. The system may also be configured to allow an independent reviewer to assess the quality of the ratings the original clinician provided. In this case, the reviewer receives all the information that the original clinician did, but annotated with information generated by a risk-based assessment system (e.g., see addendum).

The system and method described herein provides for several alternatives for independent assessment of the results of the primary clinician's report. For example, the method may include first providing the independent reviewer with the sections of the primary clinician's interview where there are discrepancies between the clinician report, patient report, and biosensors. Alternatively, method may be configured to provide priority to those sections of the interview in which the clinician changed their scores or made the most substantial or significant notes. Alternatively, the method may prioritize based on the psychometric properties of the individual scale items (as some scale items are inherently more difficult to rate accurately, i.e. more prone to error and miscalculation than other items).

The system and method may also be configured to improve Patient Reported Outcomes (PROs). These outcomes, whether electronic or on paper, are often difficult to collect in a reliable and valid manner. Also, very few clinicians take the time to appropriately explain the purpose of the questionnaire being provided to the patient or to disambiguate instructions. For example, a question "How sad did you feel this week?" with an instruction to rate 1-10, can be interpreted variously as the request to rate the highest level of sadness over the course of past week, the most recent level, or what is perceived as the average level. Patients may forget such specific instructions or not receive them at all, and in clinical research or evidence-based care, the repeated administration of these questionnaires introduces fatigue and prompts the patient to rate less carefully as more time is spent on the questionnaire. However, with current methods and systems there is no straightforward way for the clinician or anyone else to challenge these ratings, because the value in PROs lies in being independent from the clinician's assessment. These outcomes are increasingly being used to evaluate treatment program efficacy and as key secondary or co-primary outcomes in clinical trials. As a result, there is a need to improve how the data is collected from the patient According to an embodiment of the system and method disclosed herein, PROs are collected after certain embedded edit checks and prompts are encountered by the patient. These checks and prompts decrease the likelihood that the patient is careless in providing the requested information. For example, the ratings provided by the patient may be compared to the ratings provided by the patient during a previous visit, especially if the assessment is done repeatedly throughout the day or multiple times between clinical visits. The patient may take a mobile device (e.g., an ePRO device or eDiary device) home for this purpose. If there is a particular known response bias, the system may be configured to prompt the patient to confirm a certain response is intended before the response is accepted by the device. For example, rating "absent" on all symptom severity items for a patient with a chronic condition may be inconsistent or unlikely. If such a score was received, the system may be configured to generate a prompt on the device so that the patient could reconsider the score entered. The system may be configured to provide additional prompts for missing scores or impossible values before the data are finalized and submitted.

The system and method may also be configured to use the metadata about patient's interaction with a data capturing electronic device to analyze whether the data provided by the patient is likely to be inaccurate. The system may be configured so that a processor associated with the ePRO tracks when a patient changes scores, whether they change scores after reviewing earlier scores to appear more consistent, response times to particular items, and similar variables. All of the tracked variables may be integrated with the data collected from biosensors. The data may be analyzed along with external variables, such as demographics, checks for the patient being in other clinical trials databased, etc. The system may be configured to provide the clinician with a risk-based digest of the information and a guideline/recommendation about how to proceed.

FIG. 1 is a flow chart that depicts various aspects of the operation of embodiments of the system and method disclosed herein. For example, the various sources of data are disclosed being linked and time stamped prior to evaluated in the field by, for example, interviewing a patient or a clinician or at a remote clinical location ("Clinic Evaluation). The various "Activities" disclosed in FIG. 1 are supplemented, enhanced and improved by the system provided outputs and reports that are described herein.

The system may include proprietary instruments, scales or tests that have been developed to assess someone's motivation for enrolling in clinical research. The proprietary instruments may include, for example, a screening process that includes preparing a series of questions for the prospective participant that have been validated to be related to behavioral characteristics that would make a person a poor fit for a trial. The instrument can be deployed online even before a patient ever goes into a research site and at the point when they are considering enrolling in a clinical trial. The system may be configured to deploy the instrument in a self-paced, electronic environment and consists of a series of adaptive questions posed automatically and directly to the patient via prompts. The system may be configured to flag certain personality characteristics that would make treatment complicated or risky and provide that information to the clinician clinical trial. The system is configured to identify discrepancies associated with the data at various level of detail and complexity associated with a study or trial.

For example, as shown in Table 1 below risk assessments can be conducted at Levels 1-6 to detect discrepancies associated with an assessment one or more subjects or patients participating in a clinical trial or study.

TABLE 1

| Description | Example of Scores Using PANSS Scale |
|---|---|
| Level 1: Discrepancies within measure at a single subject visit | |
| This level of validation focuses on verification of the logical and psychometric relationships within a single rating scale. Data from a single assessment on one subject should demonstrate both consistent symptom presentation, as well as adherence to scoring guidelines. | Subject A at Visit X scores 1 (Absent) on P1 (Delusions) but has a score of 6 (Severe) on P5 (Grandiosity). |
| Level 2: Discrepancies across measures at a single subject visit | |
| This level of validation focuses on verification of the logical and psychometric relationships across two or more measures taken at the same subject visit. Data from multiple measures on one subject should demonstrate consistency in severity of symptoms, particularly for scales that assess similar underlying constructs. | Subject A at Visit X has a total PANSS Score of 120, demonstrating severe, acute symptomatology. The CGI-S is rated 2 (Minimal). |
| Level 3: Discrepancies across visits within subject | |
| This level of validation focuses on verification of the logical and psychometric relationships across two or more visits within a single subject. Data from single and multiple measures on one subject should demonstrate change or stability within logical boundaries. | Subject A at Visit X has a total PANSS Score of 120, demonstrating severe, acute symptomatology. At the next study visit one week later, Subject A has a total PANSS score of 60. The CGI-I is rated 4 (No Change). |
| Level 4: Discrepancies across visits between subjects | |
| This level of validation focuses on verification of the logical and psychometric relationships across two or more visits between two or more study subjects. Data from single and multiple measures on one subject should demonstrate reasonable levels of variability. | Subject A at Visit X has a total PANSS Score of 120, demonstrating severe, acute symptomatology. Subjects B, C, and D evaluated within the same week at the same site, also have total PANSS scores of 120. |
| Level 5: Patterns of discrepancies and anomalous scoring patterns within rater | |
| This level of validation focuses on patterns of scores generated by a single rater, seeking to verify consistency and accuracy in scoring. Data from single and multiple measures from one rater should demonstrate reasonable levels of variability across subjects and visits, as well as adherence to scoring guidelines. | Rater 1 has been responsible for evaluating patients A, B, C, and D on the PANSS and CGI. It is noted that at eight visits for all subjects, scores of item N3 (Poor Rapport) are always given scores of 7 (Extreme). |
| Level 6: Patterns of discrepancies and anomalous scoring within site | |
| This level of validation focuses on patterns of scores generated by two or more raters at a single site, seeking to verify consistency and accuracy in scoring. Data from single and multiple measures from two or more raters should demonstrate reasonable levels of variability across subjects and visits, as well as adherence to scoring guidelines. | Rater 1 and Rater 2 have given identical scores for 20 of 30 PANSS items on two separate subjects. | or reviewer via display or report. Certain features for assessing the patient's motivation may be derived in part from forensic literature and have been administered in the past as a pen-and-paper scale such as, for example, TOPS—Test of Psychological Symptoms. However, the present system and method configure the form for interacting with the patient electronically and integrate the patient's input with metadata relating to not only what the patient answered but also how the patient answered a question (e.g., blood pressure, etc.) thereby providing the clinician (and/or reviewer) with a multi-dimensional view of the fit of the patient to the study/treatment.

The system described herein includes a controller that may be configured to perform a risk assessment of the quality of the data and clinical review being conducted in a As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to any precise numerical ranges provided. Accordingly, these terms should be interpreted as indicating that insubstantial or inconsequential modifications or alterations of the subject matter described and claimed are considered to be within the scope of the invention as recited in the appended claims.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another.

It is important to note that the description of the system and method disclosed in the various exemplary embodiments is exemplary only. Although only a few embodiments have been described in detail in this disclosure, those skilled in the art who review this disclosure will readily appreciate that many modifications are possible without materially departing from the novel teachings and advantages of the subject matter described herein. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A system for providing improved processing of data collected during a clinical trial that includes a group of patients, wherein at least one patient is treated with a placebo, the system comprising:
    a portable electronic device configured to be operated by a clinician and/or one of the group of patients, wherein the portable electronic device is configured for collecting data related to a condition of the patient participating in the clinical trial;
    a bio sensor attached to the patient, wherein the bio sensor is configured to generate bio data representative of characteristics of the patient while the patient is participating in the clinical trial;
    a video camera configured to capture audio/video (AV) data of the patient while the patient is participating in the clinical trial; and
    a controller for processing data collected from the one of the group of patients, wherein the portable electronic device is operatively connected to the controller so that data can be transferred between the portable electronic device and the controller;
    wherein the data received from the one of the group of patients includes video data including images of the one of the group of patients;
    wherein the data includes the bio data from the bio sensor attached to one of the group of patients;
    wherein the data includes patient reported data that is captured by one of the group of patients and transmitted to the controller;
    wherein the data includes clinician data based on information inputted into the portable electronic device by the clinician in response to an interview of one of the group of patients; and
    wherein the controller is configured to process the AV data, the bio data, the patient reported data and the clinician data and produce a display of a likelihood that one of the group of patients will drop out of the clinical trial or a likelihood that one of the group of patients will respond to the placebo; and
    wherein the clinician data includes data related to an interaction of the clinician with the portable electronic device including revisions made to the clinician data by the clinician and an amount of time associated with the clinician's interaction with the portable electronic device, and wherein the controller is configured to output a report that displays both the clinician data and the AV data to thereby allow a secondary clinician to perform a quality review of the clinician data.

2. The system of claim 1, wherein the data includes secondary clinician data based on information inputted into the portable electronic device by a secondary clinician in response to a review of the AV data, the bio data and the patient reported data; and wherein the controller is configured to process the clinician data and the secondary clinician data and output a report that displays discrepancies between the secondary clinician data and the clinician data.

3. The system of claim 1, wherein the display includes, for a given point in time, both the clinician data and the AV data to thereby allow the secondary clinician to perform a quality review of the clinician data.

4. The system of claim 1, wherein the controller is configured to provide an output that includes discrepancies between the patient reported data and the bio data.

* * * * *